(12) United States Patent
Knotts

(10) Patent No.: US 12,178,744 B2
(45) Date of Patent: Dec. 31, 2024

(54) FINGERTIP WARMING DEVICE FOR INCREASING CIRCULATION

(71) Applicant: Whitney Knotts, North Charleston, SC (US)

(72) Inventor: Whitney Knotts, North Charleston, SC (US)

( * ) Notice: Subject to any disclaimer, the term of this patent is extended or adjusted under 35 U.S.C. 154(b) by 655 days.

(21) Appl. No.: 17/073,382

(22) Filed: Oct. 18, 2020

(65) Prior Publication Data

US 2022/0117778 A1 Apr. 21, 2022

(51) Int. Cl.
*A61F 7/02* (2006.01)
*A61B 5/145* (2006.01)
*A61F 7/00* (2006.01)

(52) U.S. Cl.
CPC ............ *A61F 7/02* (2013.01); *A61B 5/14532* (2013.01); *A61F 2007/0036* (2013.01); *A61F 2007/0037* (2013.01); *A61F 2007/0204* (2013.01); *A61F 2007/0219* (2013.01); *A61F 2007/0242* (2013.01); *A61F 2007/0268* (2013.01)

(58) Field of Classification Search
CPC ............ A41D 19/0003; A41D 19/0153; A61F 2007/0036; A61F 2007/0037
See application file for complete search history.

(56) References Cited

U.S. PATENT DOCUMENTS

| 5,035,003 | A | 7/1991 | Rinehart |
| 8,209,775 | B2 * | 7/2012 | Makis ................ A63B 71/141 2/163 |
| 2015/0182376 | A1 | 7/2015 | Fortner |
| 2015/0257466 | A1 | 9/2015 | Clayton |
| 2017/0086516 | A1 * | 3/2017 | Parenteau ............ A41D 13/087 |
| 2019/0029341 | A1 * | 1/2019 | Bernaz ............... A41D 19/0003 |

\* cited by examiner

*Primary Examiner* — Kaitlyn E Smith
(74) *Attorney, Agent, or Firm* — Sacejewia White; Aminah Ghaffar; NCCU IP Clinic

(57) ABSTRACT

A fingertip warming device that can be used on either hand, will aid in warming of fingertips to help increase blood flow to the fingertips of the user for the purpose of easing the process of drawing blood, which will be used to check the user's glucose levels. The device will have warming elements either embedded in the distal end of fingertip slots/compartments or allow for the use of a heatable insert that will also reside in the distal end of the device for the purpose of warming the user's fingertips. The device will provide either flaps or a hole through which the user's fingertips can be exposed to allow for collection of a blood sample for testing glucose levels.

5 Claims, 14 Drawing Sheets

FINGERTIP WARMING DEVICE FOR
INCREASING CIRCULATION

FIELD OF THE INVENTION

The present invention is related to a fingertip warming device adapted to be used on either hand of a user. In particular, the device is directed to a heatable hand covering device, wherein fingertips of a user are warmed, thereby increasing the blood flow to the fingertips of the user's hand for ease of drawing blood.

BACKGROUND

The following description is not an admission that any of the information provided herein is prior art or relevant to the present invention, or that any publication specifically or implicitly referenced is prior art. Any publications cited in this description are incorporated by reference herein. Where a definition or use of a term in an incorporated reference is inconsistent or contrary to the definition of that term provided herein, the definition of that term provided herein applies and the definition of that term in the reference does not apply.

Diabetes is a well-known and heavily researched disease that affects the human body's ability to naturally produce insulin for regulating blood sugar levels. Individuals suffering from this disease are required to regularly check their blood sugar levels by pricking their fingertips to allow for the collection of blood. The collected blood is then used to measure the individual's blood sugar levels. Depending on the blood sugar level, an individual will inject himself/herself with varying doses of insulin to adjust the sugar level and to prevent harmful results such as coma and/or death. If the user's blood sugar is out of range (low or high), the user must take immediate corrective action to bring the blood sugar in range. The user will then have to re-test blood sugar shortly thereafter (usually repeating every 15 minutes for low blood sugar until it is back in a safe range). Thus, the feature of being able to keep the other fingertips covered or re-cover quickly is key. Additionally, glucometers can malfunction as a result the user will need the ability to re-test rapidly.

The tedious process of collecting blood from the individual's fingertips is often hindered by poor circulation in the individual's fingertips. To increase blood circulation to the fingertips, warming the fingertips can increase blood flow and thereby help to provide a "better" blood sample, which would give a more accurate measure of blood sugar level for that individual. Accordingly, an individual will appreciate a device that can aid in warming his/her fingertips suffering from diabetes to increase blood circulation and thereby ease the process of blood collection and improve the quality of the blood sample.

There are several hand covering devices available in the market that warm the entire hand, and not the individual fingertips (e.g., U.S. Pat. No. 9,220,307). U.S. Pat. No. 5,035,003 also describes a glove that includes a "bladder" at the wrist and palm area of the hand. The bladder includes a liquid that can be heated and cooled, and the glove relies on gravity to circulate the liquid to either heat or cool the user's hand based on the temperature of the liquid. However, this glove does not allow exposure of a fingertip to allow for the collection of blood for testing.

U.S. Patent Application Publication 2015/0182376 describes a therapeutic glove with a removable heating pad. In one embodiment, the glove includes a thumb compartment and a finger and palm compartment. The finger and palm compartment include a pocket on the top side and on the palm side thereof. Each pocket is elongated and spans between the front end and the wrist portion of the glove. Additionally, each pocket is adapted to enclose a heating pad therein, wherein the heating pad is shaped and dimensioned similarly to the pocket. However, this glove similar to the other aforementioned invents, focuses on warming the entire hand and not just the fingertips. Amazon.com currently sells a fingerless glove with or without a mitten flap cover, wherein the core of the glove leaves the fingers of the user fully exposed. Additionally, there is an optional cover that can be used to cover the exposed fingers. However, this flap covers all the fingers in one combined flap. Sportmanguide.com also markets a fingerless glove that includes a flap that encompasses a pocket wherein a "warming pack" that provides an additional mechanism to warm the fingers. However, again, this glove does not allow for the warming of each finger individually and it requires a pair of gloves instead of the ability to use one glove that fits either hand.

Considering the aforementioned gloves, there still exists a need to have a hand covering device that can be worn, by the user, on either hand. Additionally, there is a need for a device that is configured to provide heating means for each finger and thereby increasing blood circulation to ensure the user can get

SUMMARY OF THE INVENTION

An embodiment of a fingertip warming device encompasses a proximate end, a medial portion, and a distal end. There is an opening located in the proximate end, which allows for insertion of a user's hand into said device. A palm covering is located in the medial portion of the device. The palm covering includes four finger openings which are arranged to allow each finger to be individually exposed for testing. A finger covering located is located distal end. The finger covering in the distal end has a removable heatable filer insert located in a heatable filler insert slot. There are two elongated thumb slits located on the opposite side of said medial section which allow the user to wear the device on either hand.

In a further embodiment, the fingertip warming device is constructed of linen, hemp, silk, ramie, fleece, cotton, wool, or any combination thereof. The heatable filler comprises rice, clay beads, buckwheat, or gel/gel beads or any combination thereof. The heatable insert is held in place by a covering latch and a finger covering button.

Another embodiment of a fingertip warming device encompasses a proximate end, medial end, and a distal end. There is an opening located in the proximate end, which allows for insertion of the user's hand into the device. A palm covering is located in the medial portion of the device. In still another embodiment, a finger compartment, which is located at the distal end is constructed to receive the user's fingers. There are two elongated thumb slits located on the opposite side of said medial section which allow the user to wear the device on either hand. The device has a heatable filler insert which is located in a heatable filler insert slot. The finger compartment encompasses the finger covering flap. A fastening mechanism is constructed to secure the finger covering flap in place. However, when the fastening mechanism is opened, the finger covering flap opens to expose the user's fingers for testing.

In one embodiment, the fingertip warming device is constructed of linen, hemp, silk, ramie, fleece, cotton, wool, or any combination thereof. The heatable filler insert comprises rice, clay beads, buckwheat, or gel/gel beads, cotton, wool, fleece or any combination thereof. The fastening mechanism includes a finger covering button located on the palm covering and a finger covering latch located on the finger covering flap.

A further embodiment of a fingertip warming device comprises a proximate end, medial end, and a distal end. There is an opening located in the proximate end, which allows for insertion of the user's hand into the device. A palm covering is located in the medial portion of the device. The device includes four individual finger slots located in said distal end. Each finger slot includes a corresponding fingertip flap. Each fingertip flap holds a heatable filler insert. There are two elongated thumb slits located on the opposite side of said medial section which allow the user to wear the device on either hand. wherein.

In still another embodiment, the heatable filler insert is sewn into an interior pocket within said fingertip flap. The finger slot is constructed such that once said users insert his/her hand into said device, each of the user's fingers will be inserted into the corresponding finger slot. The fingertip flap is connected to the individual finger slot via a fingertip flap hinge and the fingertip flap hinge is constructed to allow each fingertip flap to open and close independently from the other said finger flaps.

In one embodiment, the fingertip warming device is constructed of various materials, such as linen, hemp, silk, ramie, fleece, cotton, wool, or any combination thereof. The heatable filler insert is constructed of rice, clay beads, buckwheat, or gel/gel beads, cotton, wool, fleece, or any combination thereof.

DETAILED DESCRIPTION

The present invention is directed to a fingertip warming device configured to be used on either hand of a user. In particular, the device is directed to a heatable hand covering device, wherein fingertips of a user are warmed, thereby increasing the blood flow to the fingertips of the user's hand for ease of drawing blood. In one embodiment, the fingertip warming device comprises a body configured to cover four fingers of the user, heat the fingertips by utilizing heatable fillers, and allow the fingertips to be exposed through the fingertip holes via a flap integrated through the device. The heatable fillers can be made of rice, clay beads, buckwheat, or gel/gel-beads, or any combination thereof. Additionally, heatable filler inserts can be made of fleece, cotton, or any combination thereof, or any similar natural material. Furthermore, the heatable filler insert can be a disposable air activated heated insert or chemical activated gel insert.

The current disclosure describes several alternate embodiments that each can achieve the purpose of the current invention; they all provide a mechanism for warming the fingertips and increasing the blood circulation of the user's fingertips. The device can be made to accommodate hands of varying sizes. Material of construction for fingertip warming device comprises linen, hemp, silk, ramie, fleece, cotton, wool, or any combination thereof.

As used in the description herein and throughout the claims that follow, the meaning of "a," "an," and "the" includes plural reference unless the context clearly dictates otherwise. Also, as used in the description herein, the meaning of "in" includes "into" and "on" unless the context clearly dictates otherwise.

As used herein, the term "about" in conjunction with a numeral refers to a range of that numeral starting from 10% below the absolute of the numeral to 10% above the absolute of the numeral, inclusive.

As used herein, the terms "fingertip warming device" and "device" will be used interchangeably. The removable heatable filler insert can be disposable air activated heated insert or chemical activated gel insert.

Figure 1:
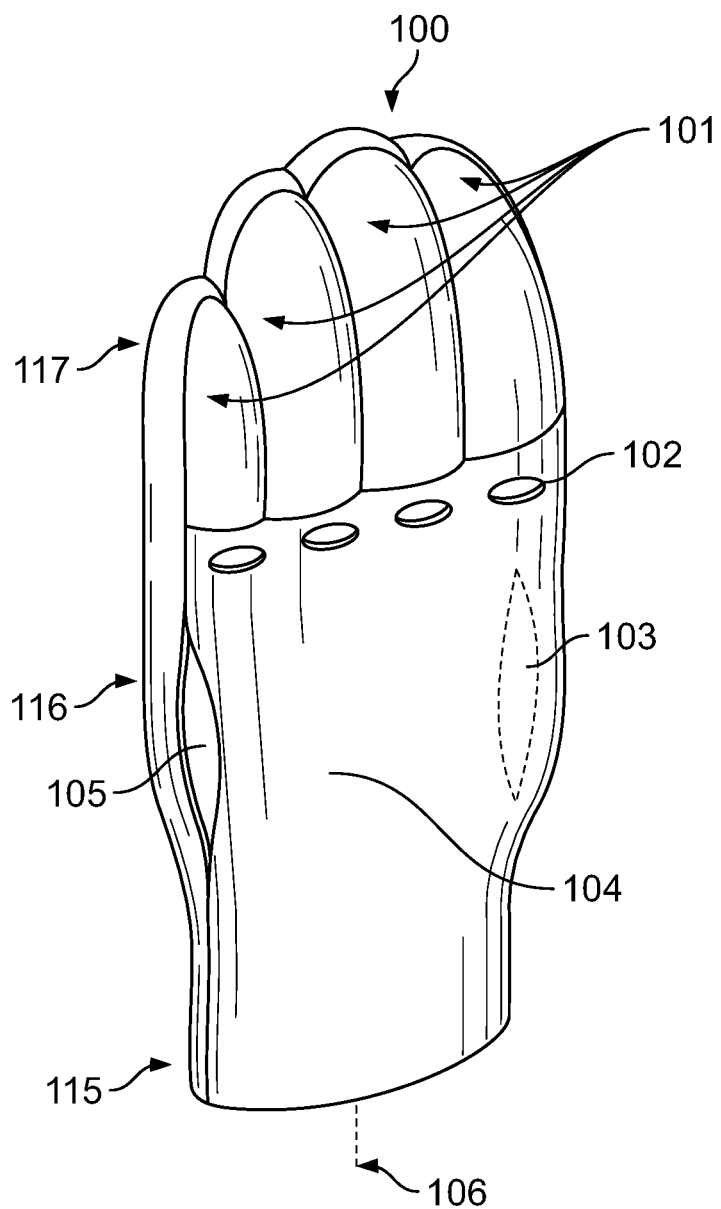
FIG. 1 is the palm side view of an embodiment of the fingertip warming device of the current invention.
Figure 2:
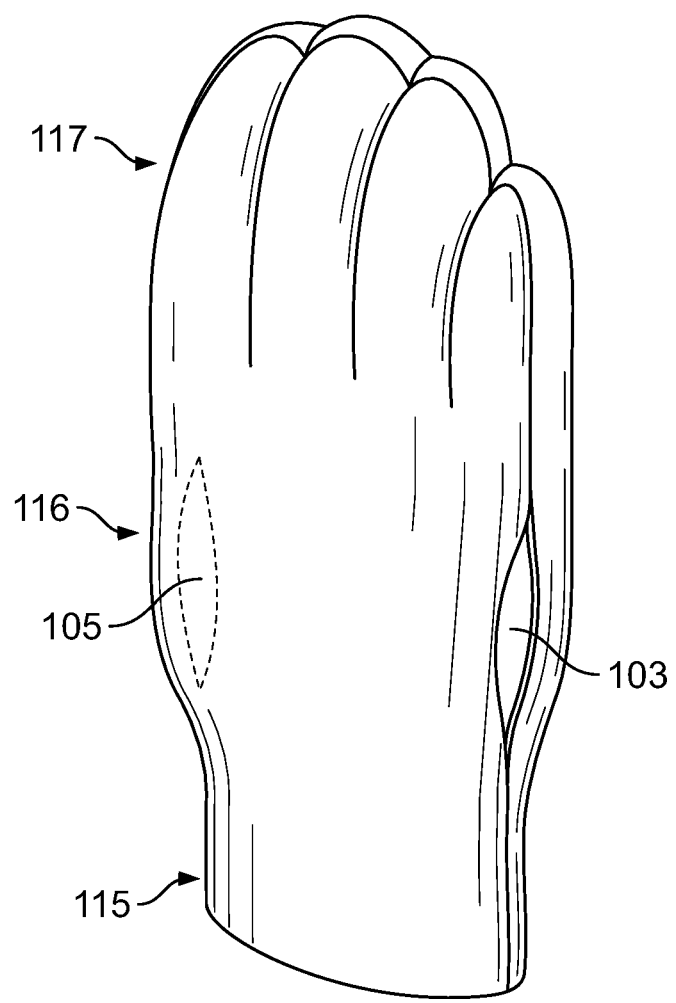
FIG. 2 is the back-hand angle view of an embodiment of the fingertip warming device of the current invention.
Figure 3:
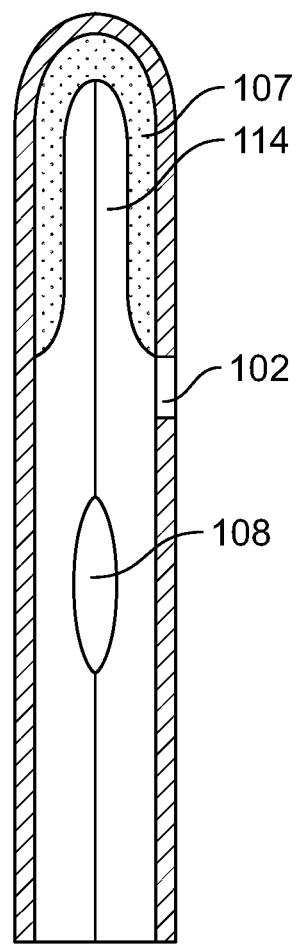
FIG. 3 is the side view cross-section showing the interior of an embodiment of the fingertip warming device of the current invention.
Figure 4:
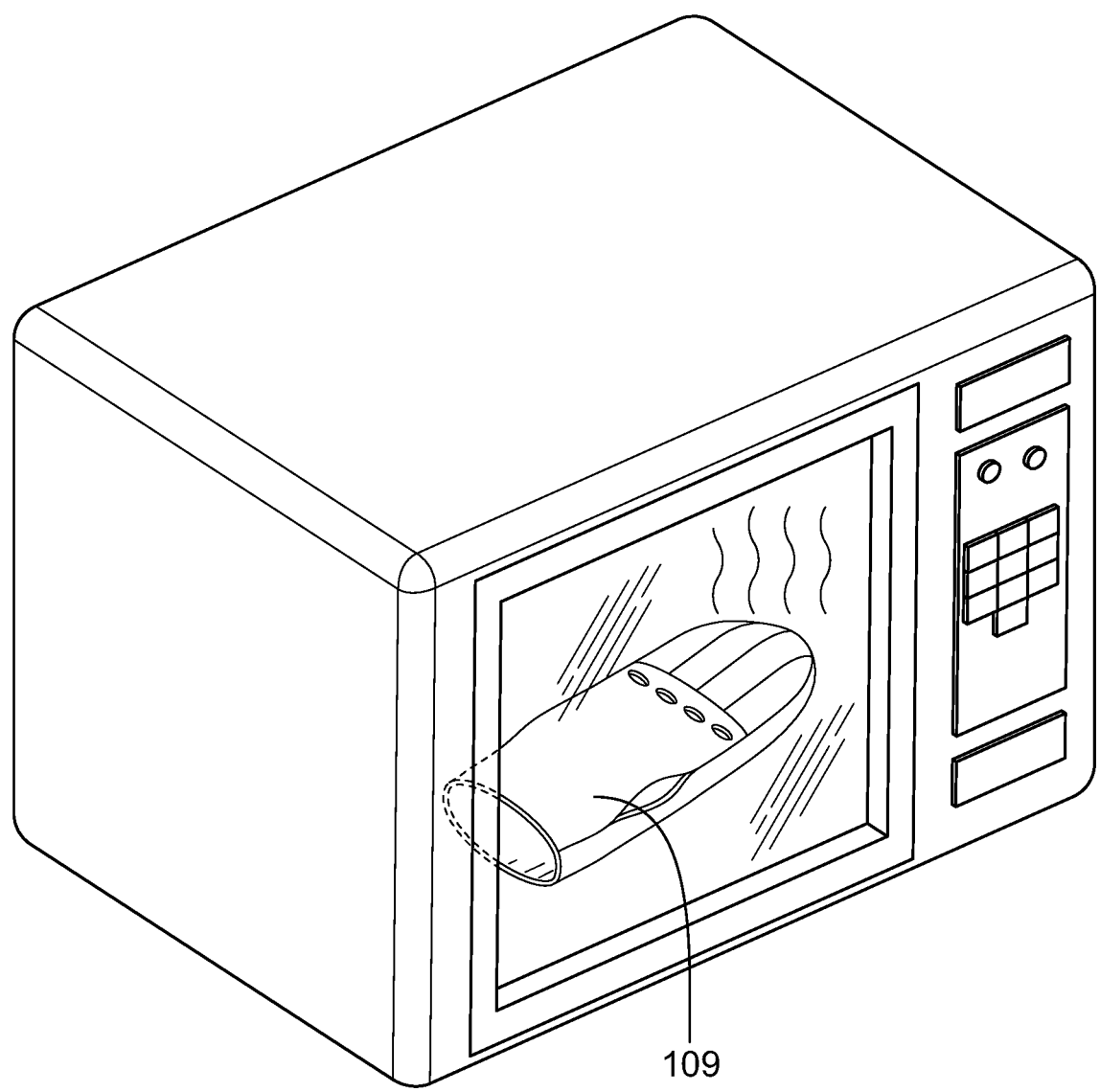
FIG. 4 depicts the method of warming an embodiment of the fingertip warming device in a microwave oven.
Figure 5:
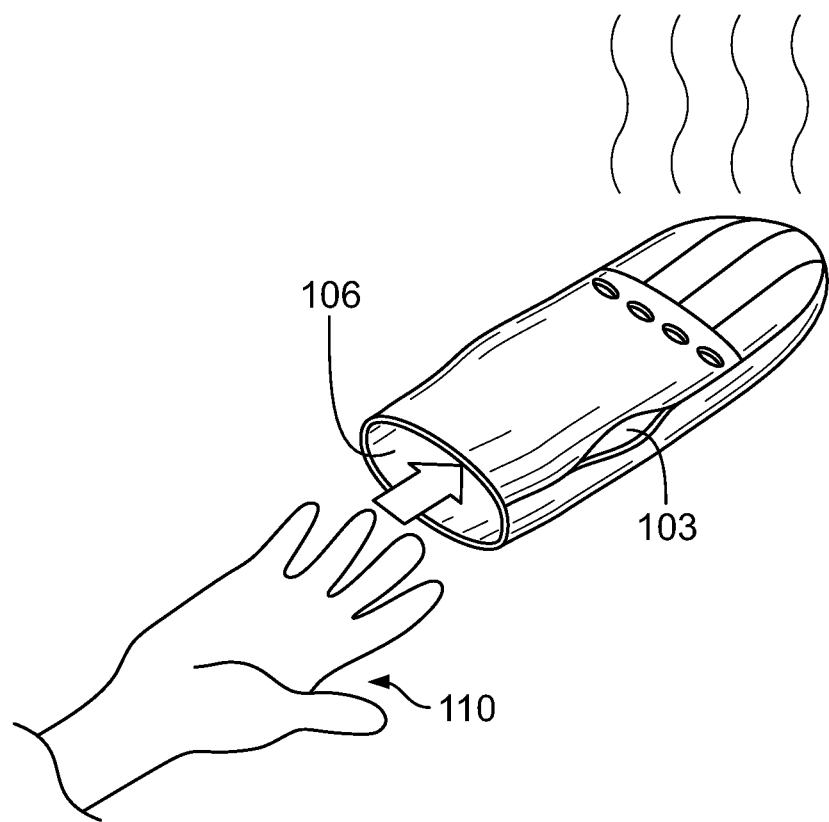
FIG. 5 depicts a method of using an embodiment of the fingertip warming device by inserting a user's right hand into the device according to the present invention.
Figure 6:
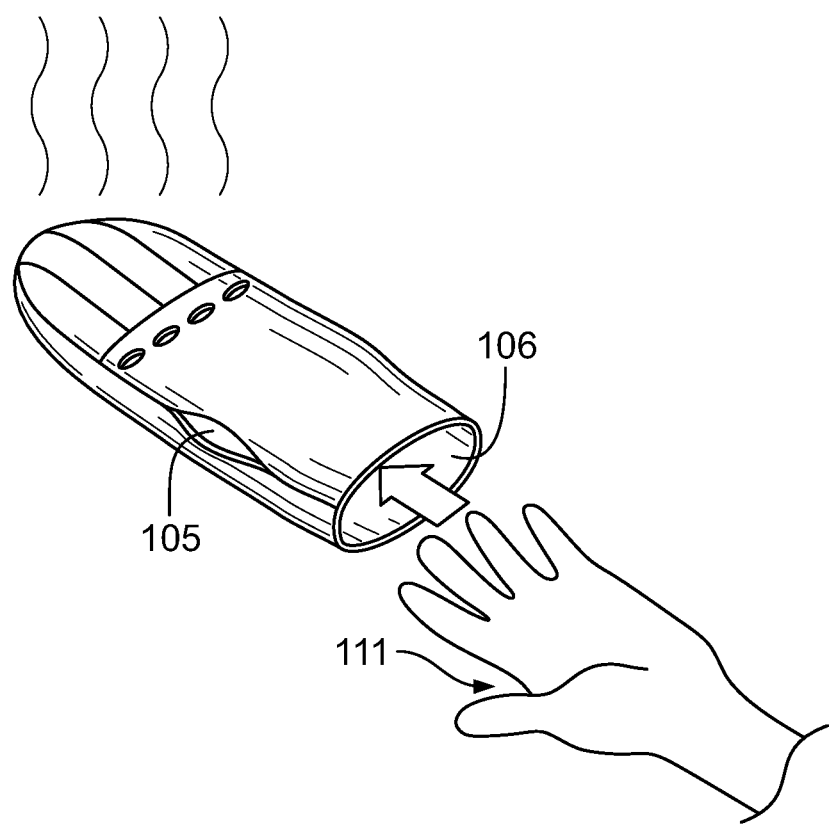
FIG. 6 depicts the method of using an embodiment of the fingertip warming device by inserting a user's left hand into the device according to the present invention.
Figure 7:
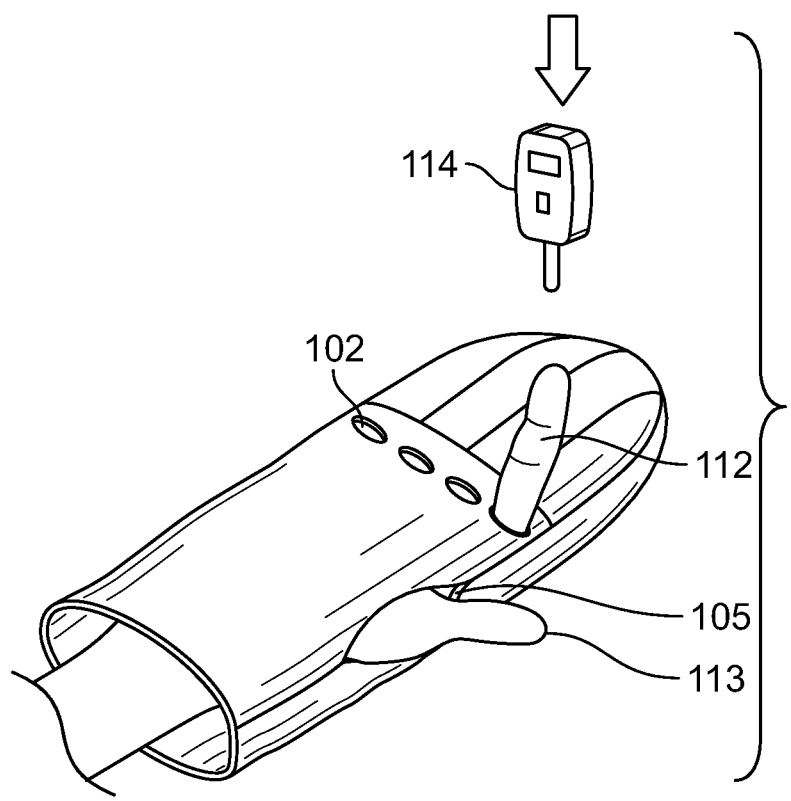
FIG. 7 depicts the method of using an embodiment of the fingertip warming device in conjunction with a glucometer.

Exemplary configurations of an embodiment of the fingertip warming device are schematically depicted in FIGS. 1-7, in which fingertip warming device 100 is designed and adapted to cover a user's hand and warm his/her fingertips to increase blood circulation and ease of collecting a blood specimen from any of the heated fingertips. Device 100 comprises a proximate end 115, medial section 116, and distal end 117, and opening 106 located in proximate end 115. In an embodiment, opening 106 is configured for inserting the user's hand into device 100. Palm covering 104 is located in medial section 116 of device 100. Device 100 further comprises four connected individual finger slots 101 located in distal end 117. Four connected individual finger slots 101 are configured to receive fingertips of the user while device 100 is in use. In one embodiment, each of connected individual finger slots 101 comprises heatable filler 107 (FIG. 3). In this embodiment, heatable filler insert 107 is encased within each finger slot in an interior pocket 114. Heatable filler 107 contacts the inner edge of each of finger slots 101 and configured to accommodate insertion of the user's fingers. In one embodiment, elongated thumb slits 103 and 105 (see FIGS. 1-2), located on the opposite side of medial section 116 of device 100, are configured to allow the user to wear device 100 on either hand. Elongated thumb slits 103 and 105 are designed to accommodate hands of various sizes to fit device 100. In one embodiment, elongated thumb slits 103 are about 2 to 4 inches in length. Palm covering 104 comprises four separate finger openings 102 designed to allow each finger 112 to be individually exposed as depicted in FIG. 7. In one embodiment, each finger opening 102 is from about 0.75 inches to about 1 inch in diameter. Accordingly, the user can expose any finger for testing by glucometer 114. To heat heatable filler insert 107, device 100 is placed into microwave oven 109 and heated for about 10 to 30 seconds. Accordingly, each heatable filler insert 107 is thereby heated; the user can then insert either right hand 110 (FIG. 5) or left hand 111 (FIG. 6) into heated device 100 by simply turning device 100 over. All four fingertips will be inserted into their corresponding finger slots 101 and heated through contact with heated filler inserts 107. The user can then individually expose any heated fingertip to be tested (FIG. 7). In one embodiment, FIG. 7 depicts how the user's thumb 113 would be exposed.

Figure 8:
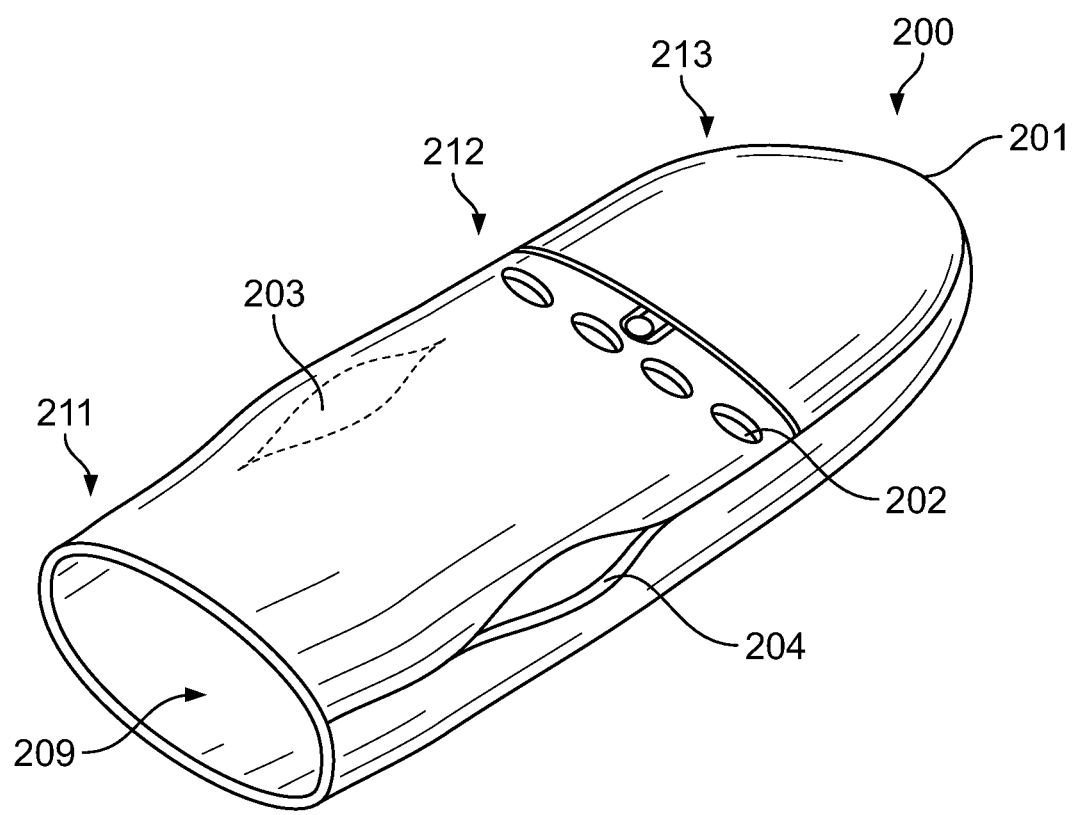
FIG. 8 is the palm side view of another embodiment of the fingertip warming device of the present invention.
Figure 9:
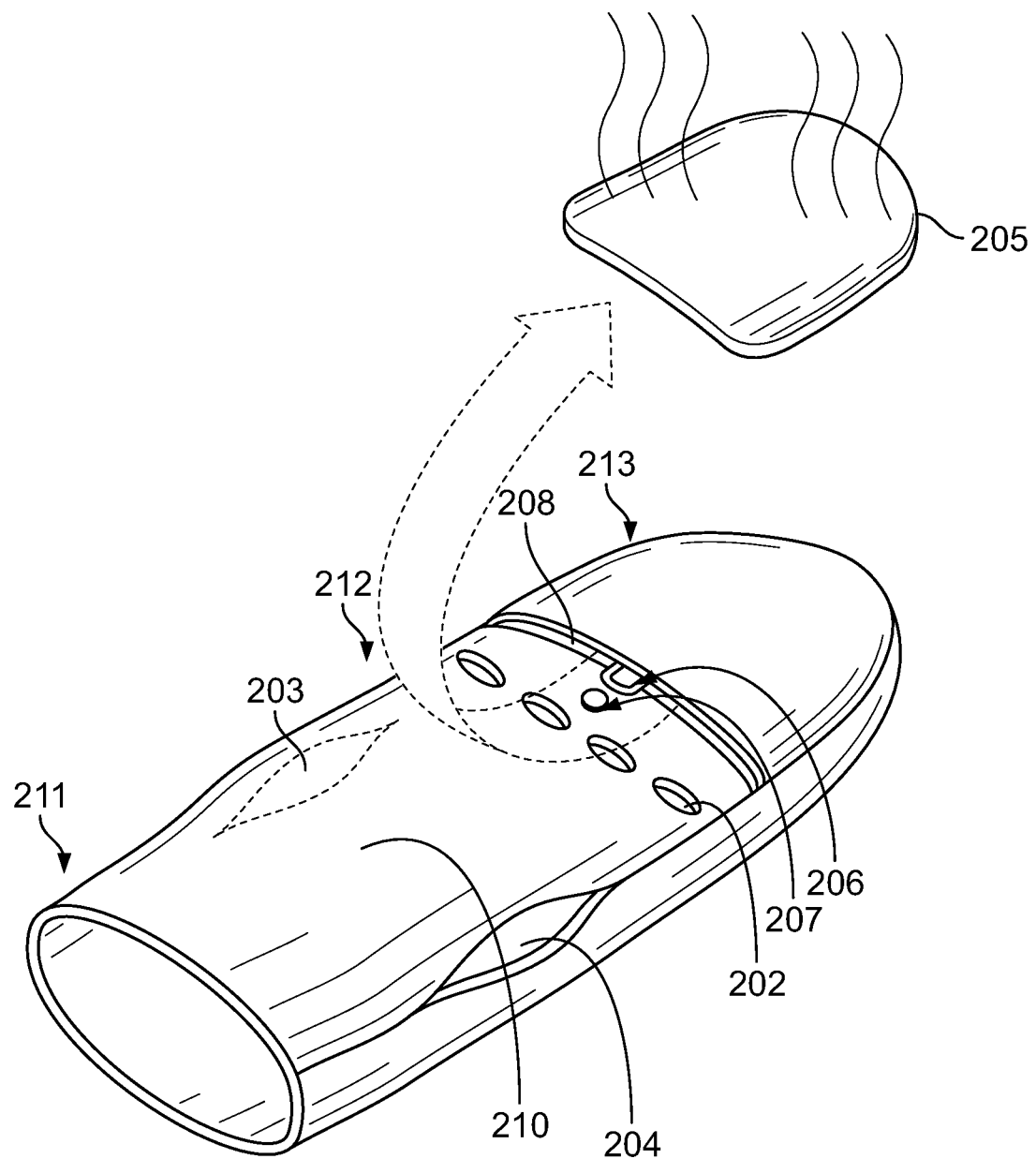
FIG. 9 depicts the method of using another embodiment of the fingertip warming device of the present invention.

Exemplary configurations of another embodiment of the fingertip warming device are schematically depicted in FIGS. 8-9, in which device 200 is designed and adapted to cover a user's hand and warm his/her fingertips to increase blood circulation and ease of collecting a blood specimen from any of the heated fingertips. Device 200 comprises proximate end 211, medial section 212, and distal end 213, and opening 209 located in proximate end 211. In an embodiment, opening 209 is configured for insertion of the user's hand into device 200. In an embodiment, palm covering 210 is located in medial section 212 of device 200 (see FIG. 9). Finger covering 201 and heatable filler insert slot 208 are located in distal end 213 of device 200. In an embodiment, palm covering 210 comprises four finger openings 202. Finger openings 202 are also configured to allow each finger to be individually exposed for testing. In one embodiment, elongated thumb slits 203 and 204 (see FIGS. 8-9), located on opposite sides of medial section 212 of device 200, and are configured to allow the user to wear device 200 on either hand. In one embodiment, thumb slits 203 and 204 are configured to accommodate hands of various sizes to fit device 200.

In this embodiment, removable heatable filler insert 205, located in heatable filler insert slot 208 (FIG. 9), allows heatable filler insert 205 to be heated separately from device 200. In one embodiment, removable heatable filler inset 205 is about 1 to 3 inches long and about 3 to 5 inches wide. In an embodiment, heatable filler insert 205 is held in place by a fastening mechanism. The fastening mechanism comprises finger covering latch 206 and finger covering button 207, wherein when finger covering button 207 is inserted into finger covering latch 206, heatable filler insert 205 is held securely in place in device 200.

The method of operation for this embodiment comprises heating removable heatable filler insert 205 into the microwave for about 10 to about 30 seconds. Alternatively, the removable heatable filler insert can be disposable air activated heated insert or chemical activated gel insert. Once the removable heatable filler insert reaches the desired temperature 90 to 110 degrees Fahrenheit, it will be inserted into the heatable filler insert slot 208 (see FIG. 9). To install the removable heatable filler insert 205 into the heatable filler insert slot 208, the user will need to unfasten the fastening mechanism, which consists of finger covering latch 206 and the finger covering button 207. Once this is done, the removable heatable filler insert 205 will be inserted into the heatable filler slot 208 and then the fastening mechanism will be fastened. At this point the user will have the ability to insert their hand into the opening 209 for the purpose of warming their fingertips. Once the user's fingertip reaches the desired temperature, the user will have the ability to expose the desired fingertip out of the corresponding finger opening 202. At this point the user can use a glucometer 114 (FIG. 7), or similarly situated device, to test the user's glucose levels.

Figure 10:
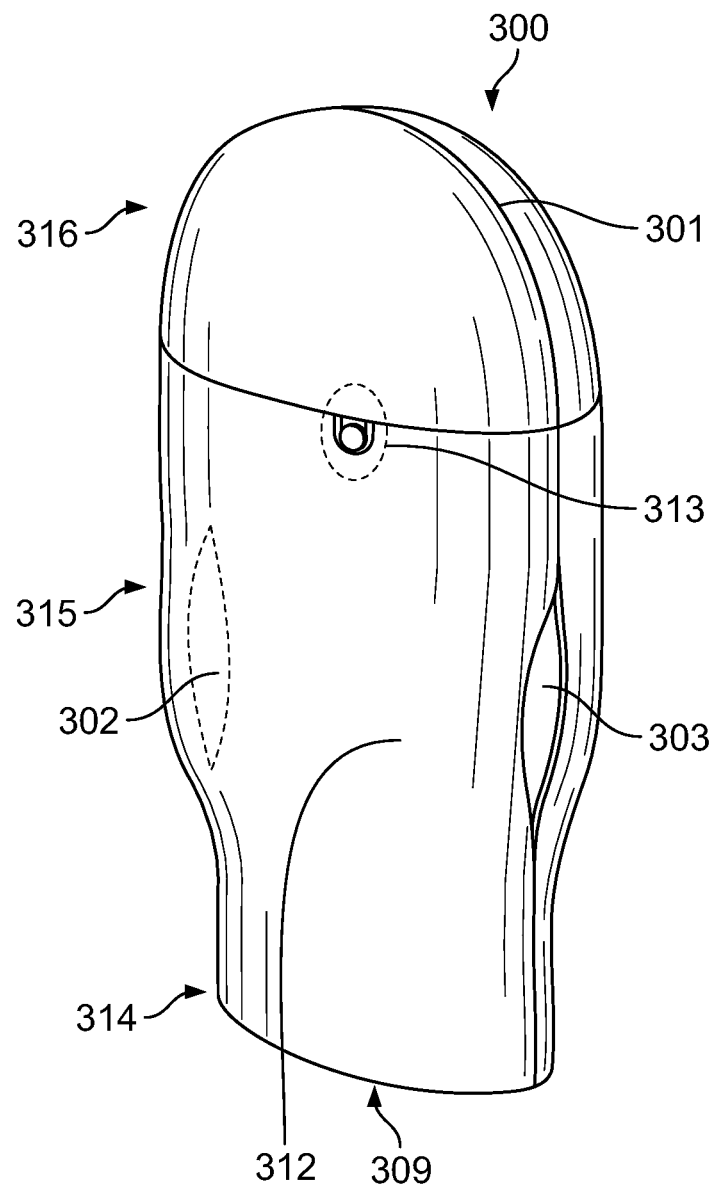
FIG. 10 depicts the palm side view of yet another embodiment of the fingertip warming device of the current invention.
Figure 11:
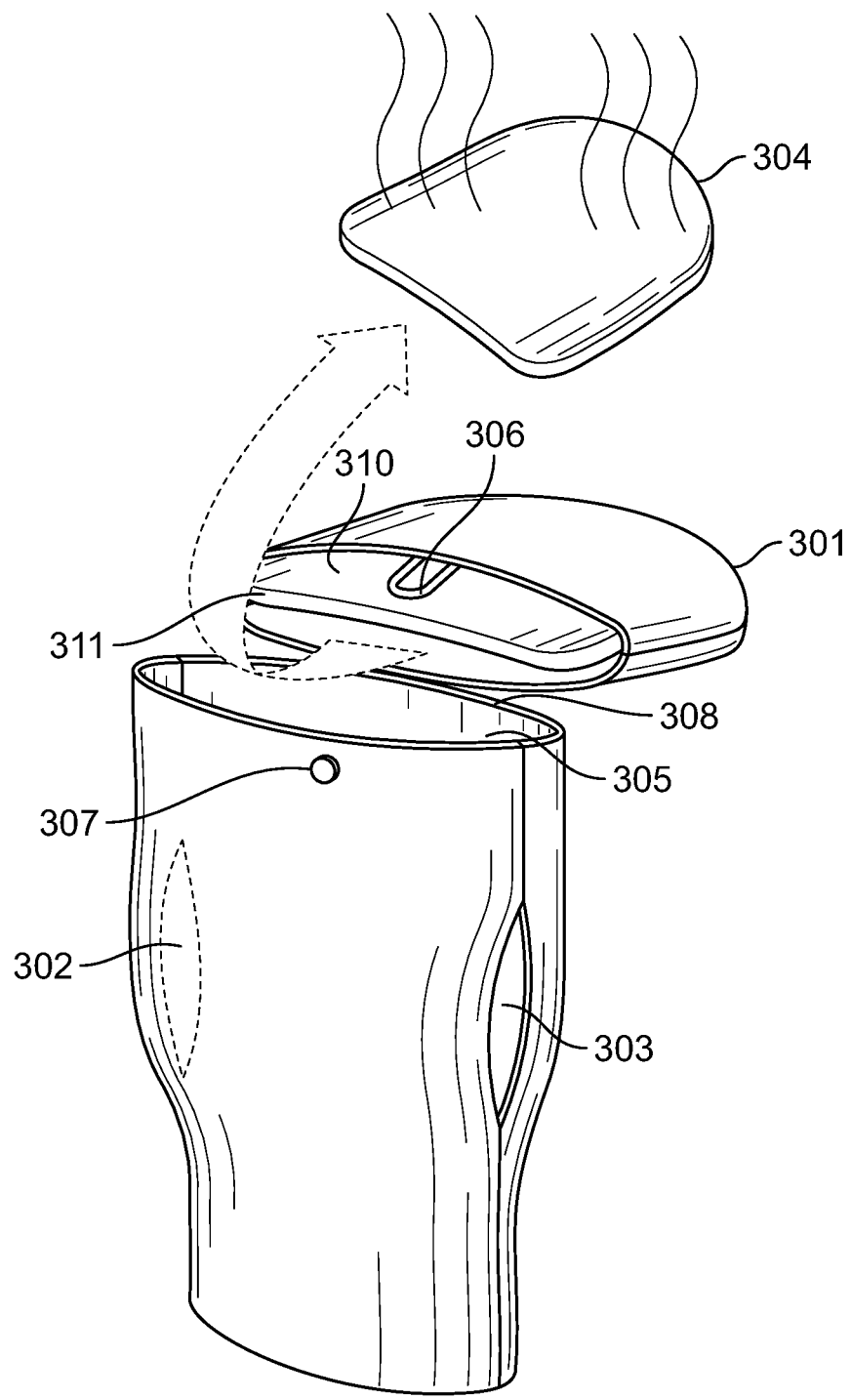
FIG. 11 depicts the method of using yet another embodiment of the fingertip warming device according to the present invention.

Exemplary configurations of yet another embodiment of the fingertip warming device are schematically depicted in FIGS. 10-11, in which device 300 is designed and adapted to cover a user's hand and warm his/her fingertips to increase blood circulation and ease of collecting a blood specimen from any of the heated fingertips. Device 300 comprises a proximate end 314, medial section 315, and distal end 316, and opening 309 located in proximate end 314. Opening 309 is configured for insertion of the user's hand into device 300. Palm covering 312 is located in medial section 315 of device 300. In one embodiment, elongated thumb slits 302 and 303 (see FIGS. 10-11) located on opposite sides of medial section 80, are configured to allow the user to wear device 300 on either hand. Device 300 further comprises finger compartment 301 which is configured to receive the user's fingers.

In an embodiment, device 300 further comprises finger covering flap 301 located in distal end 316. In this embodiment, finger covering flap 301 is connected to palm covering 312 of device 300 via finger covering flap hinge 308 configured to allow for finger covering flap 301 to open and expose the user's fingers via finger opening 305. Heat barrier 311, located inside finger covering flap 301, is configured to protect the user's fingers from extreme heat emanating from heatable filler insert 304. Heatable filler insert 304 is located in heatable filler slot 310 in the distal end of device 300. In one embodiment, heatable filler insert 304 is placed on the opposite side of heat barrier 311 away from the user's fingers inside finger covering flap 301. Heatable filler insert 304 is about 1 to 3 inches long and about 3 to 5 inches wide. Finger covering flap 301 comprises finger covering latch 306. Fastening mechanism 313 comprises finger covering button 307, located on distal end of palm covering 312, and finger covering latch 306 located on finger covering flap 301. Finger covering flap 301 is secured in place when finger covering button 307 is inserted into finger covering latch 306.

The method of operation for this device 300 comprises heating removable heatable filler insert 304 into the microwave for about 10 to about 30 seconds to reach a temperature of about 90 to about 110 degrees Fahrenheit. Alternatively, removable heatable filler insert 304 comprises a disposable air activated heated insert or a chemical activated gel insert. Once the removable heatable filler insert reaches the desired temperature, it will be inserted into heatable filler insert slot 310 (FIG. 11). The first step of installing removable heatable filler insert 304 into heatable filler insert slot 310 comprises unfastening fastening mechanism 313 that comprises, finger covering latch 306 and finger covering button 307. The second step comprises inserting removable heatable filler 304 into the heatable filler slot 310 followed by engaging fastening mechanism 313. The last step comprises the user inserting his/her hand into opening 309 (FIG. 10) to warm the user's fingertips. Once the user's fingertips reach the desired temperature, the user can expose all four fingertips, through finger opening 305. At this point the user can use a glucometer 114 (FIG. 7), or other devices, to test the user's glucose levels.

Figure 12:
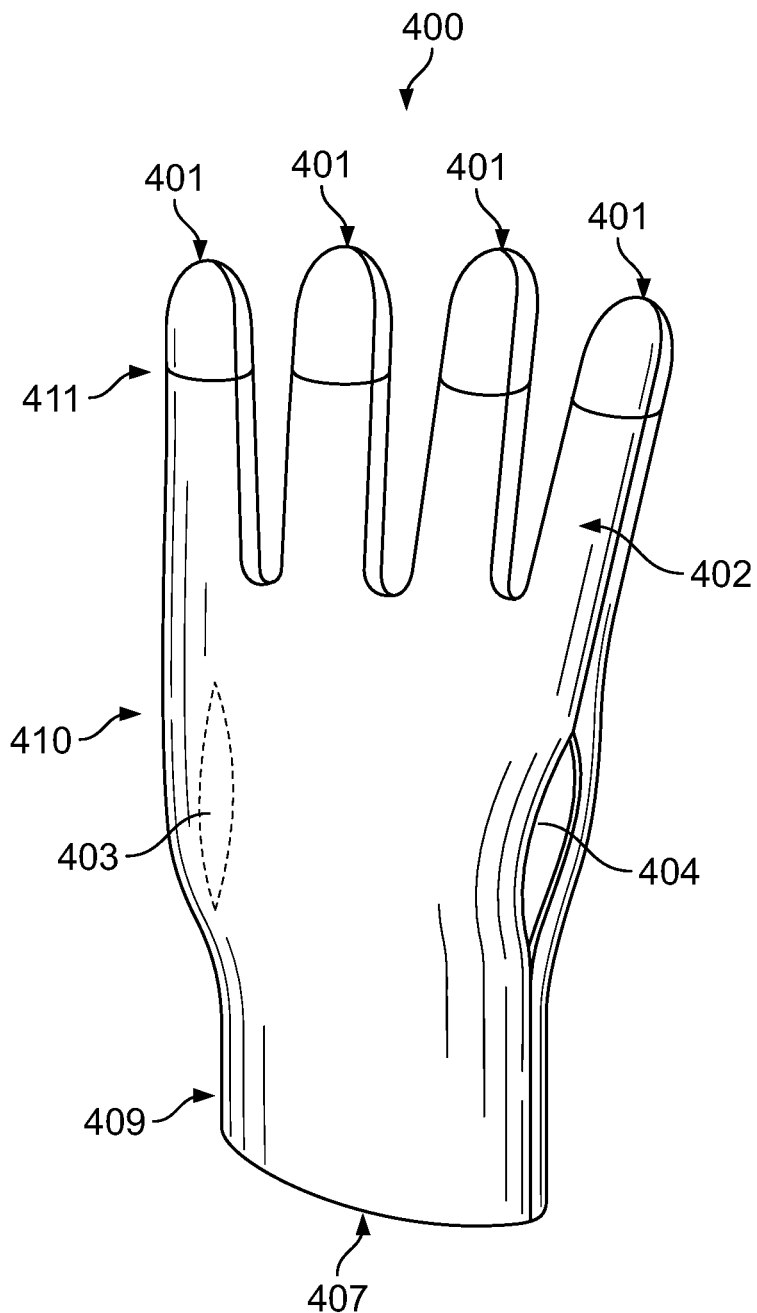
FIG. 12 depicts an alternate embodiment of the fingertip warming device of the present invention.
Figure 13:
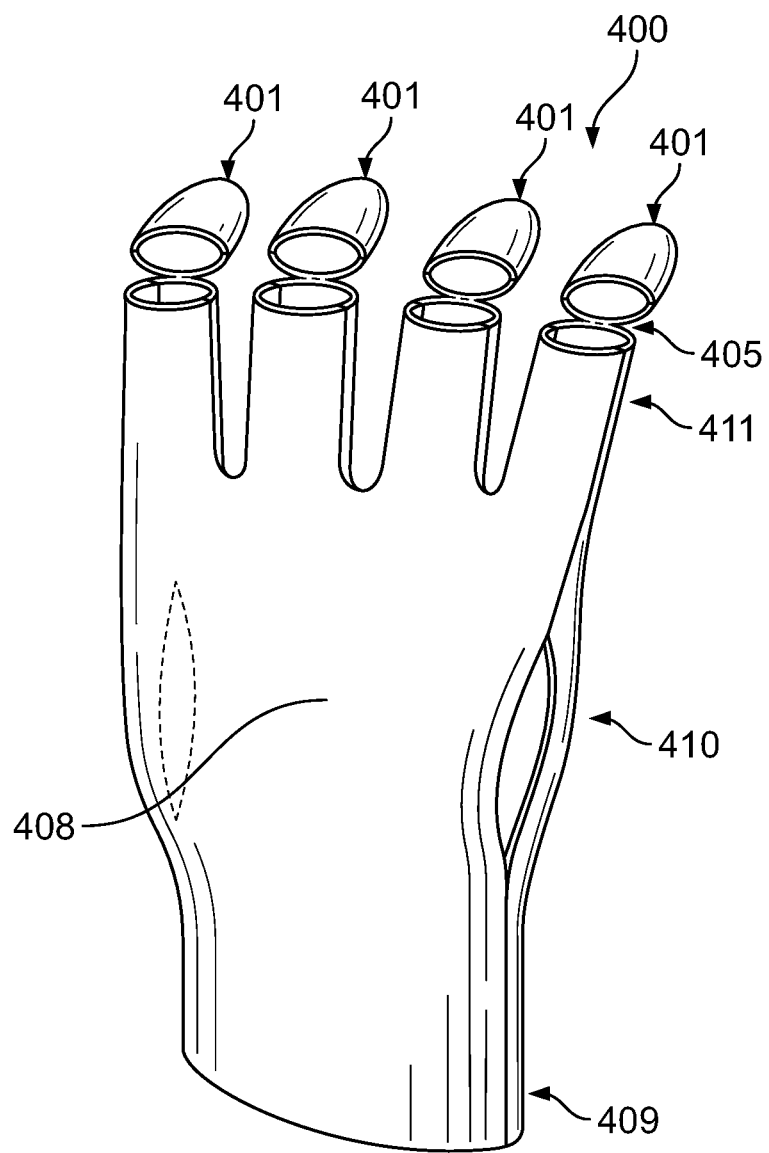
FIG. 13 depicts the palm side view alternate embodiment of the fingertip warming device illustrating the exposed fingertips configured for testing.
Figure 14:
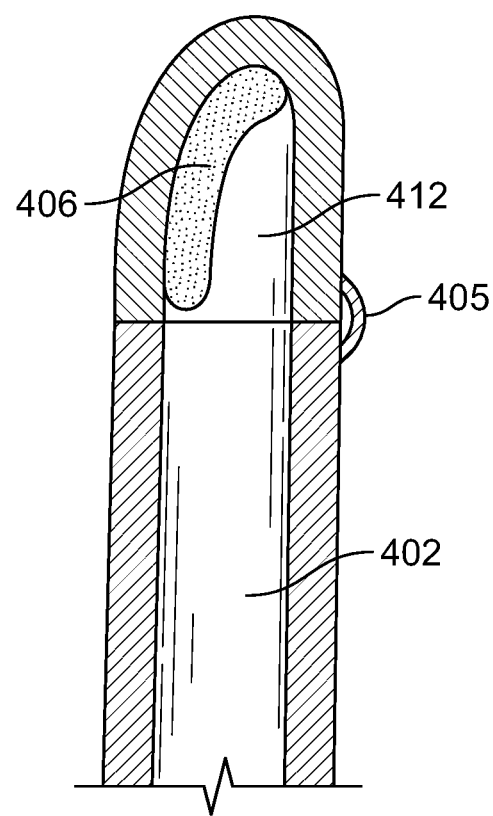
FIG. 14 depicts the cross-sectional side view showing the interior of an alternate embodiment of the fingertip warming device of the current invention.

Exemplary configurations of an alternate embodiment of the fingertip warming device are schematically depicted in FIGS. 12-14, in which device 400 is designed and adapted to cover a user's hand and warm his/her fingertips to increase blood circulation and ease of collecting a blood specimen from any of the heated fingertips. Device 400 comprises proximate end 409, medial section 410, and distal end 411, and opening 407, located in proximate end 409, which is adapted for insertion of the user's hand into device 400, palm covering 408 located in medial section 410, and two elongated slits 403 and 404. In one embodiment, elongated thumb slits 403 and 404 (see FIG. 12) located on opposite sides of medial section 410, are configured to allow the user to wear device 400 on either hand. Device 400 further comprises four individual finger slots 402, located in distal end 411, wherein each slot 402 is configured such that once the user inserts his/her hand into device 400 via opening 407, each of the user's fingers will be inserted into the corresponding finger slot 402. Each finger slot 402 comprises its corresponding individual fingertip flap 401. FIG. 12 depicts fingertip flaps 401 in a closed position. Each fingertip flap 401 is connected to individual finger slot 402 via fingertip flap hinge 405. Fingertip flap hinge 405 is configured to allow each fingertip flap 401 to open and close independently from the other finger flaps 401. FIG. 13 demonstrates flaps 401 in an open position. Each fingertip flap 401 comprises heatable filler insert 406 (FIG. 14). Heatable filler insert 406 is sewn into an interior pocket 412 within fingertip flap 401. Each heatable filler insert 406 contacts the inner edge of each of finger slots 402 and configured to accommodate insertion of the user's fingers.

The method of operation for this embodiment comprises heating device 400 into the microwave for about 10 to 30 seconds. Once device 400 reaches the desired temperature (i.e., 90 to 110 degrees Fahrenheit), the user can insert his/her hand into opening 409 for warming the fingertips which will be in direct contact with heatable filler 406. Once the user's fingertip reaches the desired temperature (i.e., 90 to 110 degrees Fahrenheit), the user can expose any fingertip by removing corresponding fingertip flap 401 to be tested. (see FIG. 7).

Thus, specific embodiments of a fingertip warming device for increasing circulation and methods to employ such device have been disclosed. It should be apparent, however, to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The invention claimed is:

1. A fingertip warming device comprising:
   (a) a proximate end, distal end, and medial section;
   (b) an opening located in said proximate end, wherein said opening is configured for insertion of a user's hand into said device;
   (c) four connected individual finger slots located at said distal end connected and unremovable from said medial section, wherein each of said connected individual finger slots is configured to receive said user's corresponding finger, wherein said four connected individual finger slots comprise a unitary system of interconnected slots and wherein said individual finger slots are not individually separable;
   (d) a palm covering located in said medial section, wherein said palm covering comprises four separate finger openings configured to allow each of said user's fingers to be individually exposed while said user's remaining fingers remain in said finger slots at said distal end; and
   (e) two elongated thumb slits located on opposite sides of said medial section, wherein said elongated thumb slits are configured to allow said user to wear said device on either hand,
   wherein each of said connected finger slots comprises a heatable filler insert and an inner edge; and
   wherein each of said heatable filler insert is configured to contact said inner edge of each of said connected finger slot.

2. The fingertip warming device of claim 1, wherein said heatable filler insert is sewn into an interior pocket within each of said connected finger slots.

3. The fingertip warming device of claim 1, wherein said connected individual finger slots are configured to receive fingertips of said user while said device is in use.

4. The fingertip warming device of claim 1, wherein said fingertip warming device is constructed of linen, hemp, silk, ramie, fleece, cotton, wool, or any combination thereof.

5. The fingertip warming device of claim 1, wherein said heatable filler insert comprises rice, clay beads, buckwheat, or gel/gel beads, cotton, wool, fleece, or any combination thereof.

* * * * *